United States Patent [19]

Kinkade

[11] Patent Number: 5,102,845
[45] Date of Patent: Apr. 7, 1992

[54] TANTALUM-CONTAINING CATALYST USEFUL FOR PRODUCING ALCOHOLS FROM SYNTHESIS GAS

[75] Inventor: Nancy E. Kinkade, Charleston, W. Va.

[73] Assignee: Union Carbide Chemicals & Plastics Technology Corporation, Danbury, Conn.

[21] Appl. No.: 655,024

[22] Filed: Feb. 14, 1991

Related U.S. Application Data

[62] Division of Ser. No. 487,504, Mar. 2, 1990, Pat. No. 4,994,498.

[51] Int. Cl.$^5$ .................. B01J 23/02; B01J 23/16; B01J 27/051
[52] U.S. Cl. .................. 502/170; 502/171; 502/220
[58] Field of Search .................. 502/170, 171, 220

[56] References Cited

U.S. PATENT DOCUMENTS 4,825,013  4/1989  Quarderer et al. ............ 502/220 X
4,831,060  5/1989  Stevens et al. ................ 502/220 X Primary Examiner—W. J. Shine
Attorney, Agent, or Firm—Gerald L. Coon

[57] ABSTRACT

A catalyst useful for selectively converting a mixture of carbon monoxide and hydrogen to a mixture of lower alkanols consisting essentially of a mixture of molybdenum sulfide, an alkali metal compound and a tantalum compound.

8 Claims, No Drawings

TANTALUM-CONTAINING CATALYST USEFUL FOR PRODUCING ALCOHOLS FROM SYNTHESIS GAS

STATEMENT OF RIGHTS

The Government of the United States has rights in the invention pursuant to Contract No. DE-AC 22-86PC90013 awarded by the U.S. Department of Energy.

This application is a division of prior U.S. application Ser. No. 07/487,504 filed on Mar. 2, 1990, now U.S. Pat. No. 4,994,498.

BACKGROUND OF THE INVENTION

1. Field of the Invention

This invention relates to a catalytic process for producing alcohols directly from carbon monoxide and hydrogen. More particularly, the present invention pertains to a tantalum and alkali-containing molybdenum sulfide heterogeneous catalyst and to its use for converting carbon monoxide and hydrogen to alcohols.

2. Description of the Related Art

Almost as old as the Fischer-Tropsch process for making hydrocarbons is the Fischer-Tropsch process for making alcohols. The reaction is carried out by passing a mixture of carbon monoxide and hydrogen over a catalyst for the hydrogenation of the carbon monoxide. A typical review article is R. B. Anderson et al., *Industrial and Engineering Chemistry*, Vol. 44, No. 10, pp. 2418-2424. This paper lists a number of catalysts containing zinc, copper, chromium, manganese, thorium, iron, occasionally promoted with alkali or other materials for making various alcohols. The authors state that ethyl alcohol is a major constituent, the yield of methanol is usually very small and a tentative summary of factors favoring the production of alcohols is high pressure, low temperature, high space velocity, high recycle ratio and carbon monoxide-rich synthesis gas.

Molybdenum (Mo), tungsten (W) and rhenium (Re) are known catalysts for the Fischer-Tropsch process, Murchison et al. in U.S. Pat. Nos. 4,151,190 and 4,199,522. The references describe some Fischer-Tropsch catalysts but do not teach that the catalyst is useful for making commercially significant quantities of alcohols. These references note that hydrogen sulfide detrimentally affects the activity of the catalyst.

Molybdenum-based catalysts have also been used to catalyze a variety of reactions such as desulfurization, denitrofication and hydrogenation reactions. For example, Stewart U.S. Pat. No. 2,490,488 discloses the use of a molybdenum sulfide catalyst promoted with "minor proportions" of an alkali metal oxide, hydroxide or carbonate to produce liquid hydrocarbons and organic oxygen-containing compounds from carbon monoxide and hydrogen. The preferred amount of the alkali promoter, according to the patent, is about 0.5 to 5 weight percent based on the weight of molybdenum sulfide, or 2-20 mole percent when the promoter is potassium hydroxide. Carbon monoxide and hydrogen are said to be converted to normally liquid hydrocarbons and unspecified organic oxygen-containing compounds utilizing such catalyst.

Frankenburg, U.S. Pat. No. 2,539,414 describes a Fischer-Tropsch process with molybdenum carbide catalysts. It teaches that the catalyst may be used to form oxygenates and at column 3, lines 66-71 teaches that one might get alcohols or hydrocarbons by varying the conditions.

More recently, Kinkade (Union Carbide), European Patent Application No. 84116467.6 (published July 24, 1985, Publ. No. 149,255) discloses that $C_{1-5}$ n-alcohols are substantially produced with a catalyst consisting essentially of molybdenum sulfide and an alkali metal compound. The gas hourly space velocity (i.e., GHSV) must be about 3000 hour$^{-1}$ or above. Variations in the GHSV, temperature, pressure and alkali metal compound are disclosed to affect the alcohol selectivity.

Quarderer et al. (Dow Chemical), U.S. Pat. No. 4,749,724 discloses that alcohols which boil in the range of motor gasoline are made at good selectivities from syngas with an optionally supported Mo/W/Re and alkali/alkaline earth element catalyst. A potassium-promoted molybdenum sulfide catalyst is most preferred, and when the catalyst is supported, carbon supports are favored. It is preferred to exclude lanthanide and actinide series metal components.

Stevens, U.S. Pat. No. 4,752,622 and Stevens et al., U.S. Pat. No. 4,752,623 (Dow Chemical), disclose catalytic processes for producing alcohols from synthesis gas over a catalyst containing as a first component Mo, W, or Re in free or combined form, and as a second component Co, Ni or Fe in free or combined form, together with an alkali or alkaline earth metal promoter.

Hucul et al., U.S. Pat. No. 4,762,858 (Dow Chemical), employs a reduced catalyst composition which includes as necessary components a catalytic metal of Nb, Ta, Mo, W, Tc, Re or a combination thereof in free or combined form with a cocatalyst of yttrium, a lanthanide or actinide series metal or a combination thereof for converting synthesis gas to predominately $C_1$ to $C_{10}$ oxygenated hydrocarbons and especially $C_1$ to $C_5$ mixed alcohols.

DETAILED DESCRIPTION

In accordance with the present invention, mixtures of alcohols are produced by reacting carbon monoxide and hydrogen over a heterogeneous catalyst consisting essentially of an intimate mixture of molybdenum sulfide, a significant amount of a compound of an alkali metal and a tantalum compound.

In a first aspect, the present invention pertains to a process which comprises reacting carbon monoxide and hydrogen in the vapor phase, in the presence of a heterogeneous catalyst consisting essentially of molybdenum sulfide, an alkali metal compound and a tantalum compound to produce a mixture of linear, $C_1$-$C_4$ alcohols at a high rate.

In another aspect, the present invention is directed to a catalyst useful for converting carbon monoxide and hydrogen to a mixture of alcohols wherein the catalyst consists essentially of an intimate mixture of molybdenum sulfide, an alkali metal compound and a tantalum compound. The alkali metal compound is present in the catalyst in an amount of at least about 0.20 mole per mole of molybdenum, and the tantalum compound is present in an amount of at least about 0.3 mole per 100 moles of molybdenum. Depending upon particular catalyst compositions, the reaction conditions of gas hourly space velocity (GHSV), temperature and pressure may be varied to obtain product alcohols at various selectivities and rates.

The presence of a small amount of a tantalum compound in prior art catalysts containing molybdenum sulfide and an alkali metal can surprisingly increase the rate at which carbon monoxide and hydrogen are converted to lower alkanols, hereinafter referred to as the alcohol production rate. As used herein, the alcohol production rate is expressed as the parts by weight of alcohol produced per unit time per part by weight of catalyst. This parameter provides a useful measure of catalyst performance. Since the catalyst is often a major part of the operating cost of the synthesis gas to alcohol conversion process and since catalyst cost varies directly with the mass of catalyst used, this parameter provides an indication of the relative economic benefits of various catalysts.

The process of the present invention converts carbon monoxide and hydrogen primarily to mixtures of linear, primary alcohols (i.e., substantially all primary alcohols with no carbon branching), containing principally one to four carbon atoms. These alcohols will be referred to in the following specification and claims as lower alkanols. Produced as minor by-products may be some longer-chain alcohols (i.e., $C_5$ and higher alcohols), some secondary and/or branched-chain alcohols, some saturated and unsaturated hydrocarbons and a small amount of aldehydes, ketones and esters. Carbon dioxide and water are other prominent by-products.

As with the prior art molybdenum sulfide and alkali metal catalyst, the catalyst used in the present invention is a relatively simple, easily-prepared composition. While many of the previously-known catalysts, which do not contain molybdenum, produce large quantities of hydrocarbons and very little alcohols, the catalyst of the present invention, like the alkali-promoted molybdenum sulfide catalyst, similarly provides a high yield of alkanols. As an additional advantage, catalysts of the present invention often exhibit an increase in catalytic activity, for the conversion of carbon monoxide and hydrogen to alkanols, i.e., an increase in the alcohol production rate, or an increase in selectivity relative to catalysts consisting of only molybdenum sulfide and an alkali metal compound.

The process of the present invention is useful for the production of mixtures of substantially linear alcohols having from 1 to 4 carbon atoms, such as methyl alcohol, ethyl alcohol, n-propyl alcohol, and n-butyl alcohol. The process may also produce minor proportions of higher alkanols and secondary and branched alcohols, such as n-pentyl alcohol and isopropyl alcohol, isobutyl alcohol, secbutyl alcohol and iso-pentyl alcohol, and hydrocarbons. The process is most useful in the production of $C_1$-$C_4$-normal alcohols. In fact, under many conditions, substantially all of the alcohol products of the process of the invention are lower alkanols.

The reaction conditions preferably are controlled to minimize by-products formation. The most prevalent by-products are hydrocarbons (both saturated and unsaturated), although the present invention generally provides a selective route to alcohols over hydrocarbons. Conditions preferably are controlled such that hydrocarbon by-products are produced in amounts, relative to total alcohol production, of less than about 25 mole %. Higher gas hourly space velocities (GHSV) tend to favor alcohol production over hydrocarbons. Small amounts of other oxygenated products such as $C_5$ and higher alcohols, secondary and/or branched-chain alcohols, and aldehydes, ketones and esters may also be produced as by-products. Such oxygenated by-products are generally produced in amounts, relative to the total alcohol production, of less than about 10 mole %, optimally less than 2-3 mole %.

According to the process of the present invention, carbon monoxide and hydrogen are reacted in the vapor phase in the presence of the solid, heterogeneous molybdenum sulfide-alkali metal catalyst containing a tantalum compound. The desired mixture of $C_1$-$C_4$-linear, primary alcohols may be separated and recovered from the gaseous reaction products and from each other by any suitable technique known to those skilled in the art. Conventional equipment may be employed in the process of the present invention, with suitable regard for the reactants, conditions of reaction and products.

The carbon monoxide and hydrogen reactants may conveniently be derived from synthesis gas which is primarily a mixture of carbon monoxide and hydrogen. Depending on its source, the reactant feed may typically contain a very small amount of sulfur compounds as well as small amounts of carbon dioxide, and nitrogen and other inert gases. Synthesis gas is produced commercially, for example, as a product of the partial combustion of coal, natural gas, petroleum bottoms or other carbonaceous materials. A specific method of synthesis gas derivation is the heating of coke in the presence of air and then steam. The molar ratio of carbon monoxide to hydrogen ($CO:H_2$) in synthesis gas may vary widely from about 1:10 to about 10:1; for purposes of the present invention, the preferred molar ratio $CO:H_2$ is from about 2:1 to about 1:4. Of course, rather than employing synthesis gas, which is the preferred reactant feed, it also is possible to use any gas containing predominantly carbon monoxide and hydrogen within the foregoing ratios. Regardless of the source of the carbon monoxide and hydrogen reactants, it is expected that the gas feed to the reaction may contain small amounts of sulfur compounds without deactivating substantially the molybdenum sulfide-alkali metal-tantalum catalyst.

The catalyst of this invention consists essentially of an intimate mixture of molybdenum sulfide, an alkali metal compound or mixture thereof and a tantalum compound or mixture thereof. The precise catalytic specie or species are not known with certainty. Operating temperatures, pressures, and catalyst preparation methods, as well as the feed gas composition, may have an effect on the structure or activity of the catalyst. The precise effects are not readily ascertainable and are difficult to measure. For this reason, it is not possible to describe with certainty the structure of the active catalytic specie or species. However, it is known that when the molybdenum sulfide precursor of such catalysts is prepared by methods described hereinbelow, it exhibits an x-ray diffraction pattern characteristic of a poorly crystalline molybdenum disulfide. X-ray diffraction characterizes only bulk crystalline phases and it is very likely that the catalyst surface contains some oxygen in addition to molybdenum and sulfur, possibly as oxythiomolybdates, for ease of description, the molybdenum nevertheless will normally be described herein as the sulfide.

Tantalum can be added to the molybdenum sulfide or to a molybdenum sulfide precursor by the so-called incipient wetness technique, well-known to those skilled in the catalyst art, and described below. Tantalum also may be added using ion exchange, by a precipitation procedure or by any other method known to those skilled in the art. A tantalum compound typically is added to the catalyst as a solution using one of its water-soluble salts, such as tantalum oxalate, or using an alcohol-soluble compound, such as tantalum ethoxide and mixtures thereof. In the broad practice of the present invention, tantalum can be added to the catalyst either before, along with or after addition of the alkali metal compound. In the presently preferred preparation procedure, described hereafter in more detail, tantalum is added to a molybdenum sulfide precursor prior to the addition of potassium.

The incipient wetness technique generally comprises adding a pore volume of solution of the desired ingredient, either a tantalum compound or an alkali metal compound, to a dry molybdenum sulfide precursor, e.g. a thiomolybdate salt, or to the molybdenum sulfide itself, preferably under vacuum, followed by drying at elevated temperature under an inert gas such as nitrogen. If the amount of tantalum compound or alkali metal compound that can be added to the molybdenum sulfide or precursor in a pore volume of liquid is less than desired because of limited solubility of the particular compound employed, the procedure may be repeated until a desired tantalum compound and/or alkali metal compound to molybdenum mole ratio is obtained.

The alkali metal compound also may be added to the molybdenum sulfide or molybdenum sulfide precursor by the so-called incipient wetness technique, or by any other method known to those skilled in the art such as ion exchange or precipitation. As with the tantalum compound, the alkali metal compound normally is added to the catalyst as a solution generally using a water-soluble salt such as potassium acetate. In the presently preferred preparation procedure, the alkali metal compound, most preferably a potassium compound, is added to a tantalum-containing molybdenum sulfide.

The particular alkali metal compound contained in the catalyst of the invention may have an effect upon the activity and alcohol selectivity of that catalyst. Generally, suitable alkali metal compounds may be selected from inorganic and organic salts, hydroxides, oxides and sulfides of alkali metals and mixtures thereof. It is expected that most organic and inorganic salts of alkali metals will form catalysts for enhancing the conversion of synthesis gas to alcohols. Examples of suitable inorganic salts are the nitrates, sulfates and carbonates of the alkali metals (e.g. sodium, potassium, lithium, cesium and rubidium); examples of suitable organic salts are the acetates, citrates, tartrates, methoxides and ethoxides of the alkali metals.

Specific examples of suitable alkali metal compounds useful in this invention include potassium hydroxide, potassium acetate, potassium nitrate, cesium sulfate, cesium acetate, lithium nitrate, sodium nitrate, rubidium acetate, and the like. The hydroxides, acetates and sulfates are preferred. Among the various alkali metals, the potassium, cesium and rubidium compounds are preferred. Particularly preferred compounds are potassium hydroxide, potassium acetate, cesium acetate and cesium sulfate, especially potassium acetate.

The form of the alkali metal and/or tantalum in the active catalyst may not be the same as the tantalum compound and/or alkali metal compound that was introduced to the molybdenum sulfide or molybdenum sulfide precursor during catalyst preparation. For purposes of the present invention, it is sufficient if the tantalum compound and/or alkali metal compound is added as described herein, regardless of the particular form it may subsequently take in the active catalyst. In terms of the present invention, the resulting catalyst is said to consist essentially of an intimate mixture of molybdenum sulfide, an alkali metal compound or mixture thereof, and a tantalum compound, or mixture thereof.

The minimum amounts of tantalum compound and alkali metal compound in the catalyst should be that amount necessary to provide a high level of catalytic activity, and preferably those amounts necessary for producing more alcohols than hydrocarbons. The amounts will vary depending upon the particular alkali metal compound and tantalum compound and the reaction conditions; but can be determined using no more than routine experimentation.

As low as about 0.20 mole of alkali metal per mole of molybdenum can be used if certain preferred alkali metal compounds (e.g. potassium, rubidium or cesium compounds) are employed and/or if reaction conditions are selected which favor alcohol production over hydrocarbons (e.g. higher GHSV's, higher pressures and lower temperatures). The preferred lower limit of alkali metal in the catalyst is about 0.30 mole of alkali metal per mole of molybdenum. The upper limit of the amount of alkali metal compound in the catalyst is not absolutely fixed and amounts as high as about 2 moles of alkali metal per mole of molybdenum can usually be used with good results. Therefore, as a general rule, amounts of alkali metal compound to provide from about 0.30 to about 2 moles of alkali metal per mole of molybdenum may be employed in the present invention. It is preferred, however, that the catalyst contain from about 0.30 to about 0.80 mole of alkali metal per mole of molybdenum.

Amounts of tantalum as low as 0.3 mole per 100 moles of molybdenum can be used in the broad practice of the present invention. Preferably, at least 0.6 mole of tantalum per 100 moles of molybdenum is used. While an upper limit on the amount of added tantalum compound has not been specifically defined, it is expected that a level which provides above about 10 moles of tantalum per 100 moles of molybdenum should not be necessary to obtain optimum results. Most preferably, between about 0.7 mole and 5 moles of tantalum per 100 moles of molybdenum is used.

The catalyst may be prepared by conventional means, such as by adding a tantalum compound and an alkali metal compound to a sulfur-containing molybdenum compound such as $MoS_3$, $MoS_2$, ammonium oxythiomolybdate or ammonium polythiomolybdate (which compounds may be obtained commercially or prepared from a variety of molybdenum compounds). Addition of the tantalum and alkali metal may be accomplished by impregnation with a solution of the tantalum compound and alkali metal compound (e.g. by an incipient wetness technique), by co-precipitation, by grinding and calcining a dry tantalum compound and an alkali metal compound with the molybdenum compound, by ion exchange or by other known procedures which provide an intimate mixture of the catalytic components.

Another method of preparing the catalyst comprises sulfiding a commercially-available alkali metal molybdate or a molybdenum oxide such as $MoO_3$ or $MoO_2$, after treatment with an alkali compound, followed by impregnation with a tantalum compound.

A particularly preferred method of preparing the catalyst of the present invention comprises decomposing a tantalum-impregnated thiomolybdate salt to produce a tantalum-loaded molybdenum sulfide, (a method for thiomolybdate decomposition is described in U.S. Pat. Nos. 4,243,553 and 4,243,554), and then adding the alkali metal compound to the tantalum-loaded molybdenum sulfide by any suitable technique, such as by the incipient wetness method, and then, if desired, calcining the catalyst after addition of the alkali metal. Calcination can be effected by heating the catalyst in a tube furnace at a gradually increasing temperature (10° C./min) up to 400° C. under a flow of 20 parts, by volume, hydrogen and 180 parts by volume nitrogen, and holding the catalyst at 400° C. for one hour. This method is preferred since it has been observed to produce a more active catalyst for the production of lower alkanols expressed on the basis of catalyst mass, than the same type of catalyst prepared by the other enumerated techniques.

More specifically, in a preferred method, a tantalum-loaded molybdenum sulfide may be prepared by decomposing a tantalum-loaded thiomolybdate salt, such as ammonium tetrathiomolybdate ("ATM") or ammonium polythiomolybdate, at an elevated temperature (e.g. on the order of 300°-600° C.) in a gaseous atmosphere such as nitrogen or hydrogen or mixtures thereof. Other gases may be employed, such as an inert gas, and carbon monoxide.

The ammonium thiomolybdate or other salt may be prepared by known methods, such as (in the case of ammonium tetrathiomolybdate) by bubbling hydrogen sulfide through an ammonium hydroxide solution of ammonium hepta molybdate, $(NH_4)_6Mo_7O_{24} \cdot 4H_2O$, at elevated temperatures (e.g. 30°-40° C.). The tantalum compound then is added to the thiomolybdate salt, such as by the incipient wetness technique or more preferably by adding the tantalum compound as a solution with a large excess of solvent, e.g. water or an alcohol, and the impregnated salt is then decomposed as indicated above. The alkali metal compound then is added to the decomposed, tantalum-loaded molybdenum sulfide. The alkali metal compound may be introduced by the incipient wetness technique. This preferred preparation procedure has been observed to produce lower density catalysts with enhanced activity, expressed on the basis of catalyst mass, for converting synthesis gas to alcohols. In addition to the preparation procedures, catalyst density also is influenced by the scale of production, level of potassium loading, drying conditions and the like. Catalysts having densities below 1.0 gram per cubic centimeter, and particularly below 0.8 gm/cc have shown the highest alcohol production rates, and thus are presently preferred.

The catalyst of the present invention may be employed in any convenient solid form depending upon the conditions of reaction and the equipment employed. For example, the catalyst, normally obtained as a powder may be made into other conventional forms such as pellets, tablets, granules, or may be supported on any suitable inert support. In the case of fluidized-bed operations, a powdered catalyst of suitable size may be appropriate. Those skilled in the art will be able to practice the invention by selecting the form and size of catalyst, based on the conditions encountered in use. If a supported catalyst is desired, any typical inert support may be employed, such as carbon, silica, alumina, titania, silica-alumina, silica-titania, magnesia, molecular sieves and zeolites, and clays.

The supported catalysts may be prepared by conventional techniques analogous to those employed for the unsupported catalysts, such as an incipient wetness technique using ammonium hepta molybdate, tantalum oxalate and potassium acetate in aqueous solution. Supported catalysts or pelletized or extruded unsupported catalysts are favored in large-scale, fixed-bed systems. Slurry systems are conveniently operated with finer catalyst particles. The use and selection of supported or unsupported catalyst systems to suit various reactor systems is readily understood by those skilled in the art.

To produce the desired mixture of lower alkanols, the carbon monoxide and hydrogen feed are reacted in the vapor phase in suitable equipment, in the presence of the catalyst, under suitable conditions of gas hourly space velocity (GHSV), temperature and pressure.

The GHSV of the feed gas is defined as the volume of gas fed per volume of catalyst charge per hour (expressed as reciprocal hours, $hr^{-1}$) and high GHSV's result in high selectivities to the desired alcohols. For purposes of the present invention, the GHSV should be at least about 1500 $hr^{-1}$, preferably at least about 3000 $hr^{-1}$. With lower GHSV's, hydrocarbon selectivity may increase at the expense of alcohol selectivity. There is no known maximum GHSV and it will depend in part on the economics of the equipment used. With GHSV's much higher than about 12,000 $hr^{-1}$, alcohol selectivity is not substantially changed and while the rate of alcohol production may generally increase with higher GHSV's the total conversion to product may decrease slightly.

The temperature at which the process of the invention may be performed is not particularly critical and may be varied depending on the results desired. As a general rule, the temperature of the process may be from about 250° C. to about 400° C., and a temperature of from about 275° C. to about 350° C. is preferred. When higher temperatures are used, a larger proportion of hydrocarbons may be also produced. Therefore, depending on the particular catalyst and the desired results, the reaction conditions may be varied.

The pressure of the reaction is not critical and may be from about atmospheric to about 2,000 psig, depending on the equipment used and results desired. Generally, increasing pressure tends to favor alcohols over hydrocarbons and may also favor shorter-chain products.

The product alkanols have many and varied industrial uses. For example, they are useful as solvents and also as intermediates for the production of, for example, plasticizers for synthetic resins or as fuel additives.

The examples which follow are meant to further illustrate the present invention. Unless otherwise noted, the following procedures were employed in all of the Examples.

CATALYST PREPARATION

Except as noted in the examples, the molybdenum sulfide catalysts were all prepared by decomposing ammonium tetrathiomolybdate (ATM) at an elevated temperature, usually about 400° C., in nitrogen containing 10 volume percent hydrogen. The ammonium tetrathiomolybdate was prepared by bubbling hydrogen sulfide through an ammonium hydroxide solution of ammonium heptamolybdate, $(NH_4)_6Mo_7O_{24} \cdot 4H_2O$, at 30°-40° C. The molybdenum sulfide prepared in this manner exhibited an x-ray diffraction pattern typical of molybdenum disulfide and surface areas of 10-100 $m^2/g$.

The tantalum and alkali metal compound additives were introduced into the molybdenum sulfide either by an incipient wetness technique (IW) or by using a large excess of solvent (ES). Specifically, according to the incipient wetness procedure a solution of the tantalum compound or the alkali metal compound was introduced onto the molybdenum sulfide precursor (ATM) before its decomposition or thereafter onto the resulting molybdenum sulfide (decomposed ATM) and stirred with a spatula to wet the powder completely. The resulting wet material was allowed to stand for about 30 minutes or more and then dried in a tube furnace or in a vacuum oven under a flow of nitrogen at 110° C. for 2 hours or overnight. When using the incipient wetness technique, the volume of the solution added was equivalent to one pore volume of the ATM or the molybdenum sulfide, i.e., the volume required to fill the void volume of the ATM or the molybdenum sulfide.

In the excess solvent approach, the tantalum compound or alkali metal compound is dissolved in the solvent, e.g. distilled water or ethanol, as appropriate, in an amount well in excess of one pore volume, and stirred with the molybdenum sulfide or precursor (ATM) for about 24 hours and then dried as above.

Tantalum was added in various amounts either as an aqueous tantalum oxalate solution or an alcoholic tantalum ethoxide solution. Potassium was added in various amounts as an aqueous solution of potassium acetate.

The final dried catalyst was then ground to a powder and added to a tube furnace and calcined (or decomposed if not done earlier) at a gradually increasing temperature (10° C./min) up to 400° C. under a flow of 20 parts by volume of hydrogen and 180 parts by volume of nitrogen. After one hour at 400° C., the hydrogen flow was stopped and the material cooled to ambient temperature. Since in all cases the catalyst may be pyrophoric, it was passivated after all steps of calcination at 400° C. with a mixture of nitrogen and air by gradually increasing the mixture's air content from 0 volume % to 100 volume % over a 1.25-hour period prior to its use for catalyzing the syn-gas conversion reaction.

SYNTHESIS GAS CONVERSION

The reactor used in the examples was a continuous feed, U-shaped, stainless steel, tubular reactor with no recycle. Gas samples were routinely analyzed on-line by conventional gas chromatographic (GC) techniques. A mass spectrometer was used initially to identify the products, e.g. hydrocarbons, alcohols, hydrogen, carbon monoxide and carbon dioxide isolated by GC. The catalyst was loaded into the stainless steel U-tube with 0.5 mm quartz beads above and below the catalyst bed. Catalyst was prepared as powder and then mixed with an equal volume of 0.5 mm quartz beads. Once installed, the reactor was pressure tested and then flushed several times with nitrogen before the reactant gas mixture (carbon monoxide and hydrogen) flow was started. After the reactor was heated to reaction temperature in a fluidized sand bath, the desired flow and pressure were established. A synthesis gas containing CO and $H_2$ at a molar ratio of 1:1 was flowed through the catalyst bed at a GHSV of 6000 $hr^{-1}$, at a temperature of 300° C. and at a pressure of 1200 psig. Product gas analysis was performed every two hours, and liquid product was collected once or twice a day. The reactor was cooled to room temperature after each run with a slow flow of nitrogen passing through the catalyst, followed by depressurization.

As a basis of comparison, optimized prior art catalyst compositions free of tantalum and consisting essentially of molybdenum sulfide and an alkali metal compound were prepared and tested for converting synthesis gas to alcohol. The catalysts were prepared by impregnating molybdenum sulfide, made by decomposing ammonium tetramolybdate (ATM) as described above, with potassium acetate to provide 0.75 mole K per mole Mo via the incipient wetness technique. All other conditions of preparation and use are the same as outlined above. The results of testing these optimized prior art catalysts for synthesis conversion are reported below in Table A.

Selectivity to $C_1$-$C_4$ linear alcohols is reported in the following tables and examples as the number of moles of carbon in such alcohols as a percentage of the total number of moles of carbon in all products, excluding $CO_2$.

TABLE A

| Catalyst No. | Density (g/cc) | Alcohol Selectivity (%) | Alcohol Production Rate (lb alcohol/hr/lb catalyst) |
| --- | --- | --- | --- |
| A1 | 1.01 | 75 | 0.30 |
| A2 | 1.13 | 70 | 0.28 |
| A3 | 0.99 | 74 | 0.30 |
| A4 | 0.82 | 74 | 0.33 |
| Average | 0.99 | 73.3 | 0.30 |

EXAMPLE 1

A catalyst was prepared by impregnating molybdenum sulfide (decomposed ATM) first with an aqueous solution of tantalum oxalate then with an aqueous solution of potassium acetate, both via the incipient wetness procedure to provide 8.9 moles Ta per 100 moles Mo and 0.75 mole K per mole Mo. The catalyst was calcined after potassium impregnation. The catalyst exhibited a density of 1.32 g/cc a selectivity of about 70% and an alcohol production rate of 0.25 pound of alcohol per hour per pound of catalyst.

EXAMPLES 2 AND 3

Two catalysts were prepared by impregnating ATM sequentially with an ethanol solution of tantalum ethoxide and an aqueous potassium acetate solution, both using the incipient wetness technique; followed by decomposition of the tantalum and potassium impregnated ATM. The catalyst of Example 2 had 0.82 mole Ta per 100 moles Mo and 0.75 mole K per mole Mo; while the catalyst of Example 3 had 0.83 mole Ta per 100 moles Mo and 1.22 moles K per mole Mo. Test results are summarized in Table 1.

TABLE 1

| Catalyst No. | Density (g/cc) | Alcohol Selectivity (%) | Alcohol Production Rate (lb alcohol/hr/lb catalyst) |
| --- | --- | --- | --- |
| 2 | 0.85 | 77 | 0.28 |
| 3 | 0.99 | 71 | 0.24 |

EXAMPLES 4 AND 5

Two catalysts were prepared by adding an aqueous solution of tantalum oxalate to ATM using the excess solvent technique in an amount to provide 0.87 mole Ta and 4.3 moles Ta per 100 moles Mo respectively, followed by impregnation with aqueous potassium acetate to provide 0.73 mole K per mole Mo via incipient wetness. The tantalum and potassium impregnated ATM was then decomposed. Test results are summarized in Table 2.

TABLE 2

| Catalyst No. | Density (g/cc) | Alcohol Selectivity (%) | Alcohol Production Rate (lb alcohol/hr/lb catalyst) |
|---|---|---|---|
| 4 | 1.27 | 72 | 0.19 |
| 5 | 1.20 | 75 | 0.23 |

EXAMPLES 6-8

Three catalysts were prepared by adding an ethanol solution of tantalum ethoxide to ATM using the excess solvent procedure in an amount to provide 0.83 mole Ta per 100 moles Mo; followed by adding an aqueous solution of potassium acetate via incipient wetness, and decomposing the tantalum and potassium impregnated ATM. Test results are summarized in Table 3.

TABLE 3

| Catalyst No. | Potassium (mole K/mole Mo) | Density (g/cc) | Alcohol Selectivity (%) | Alcohol Production Rate (lb alcohol hr/lb catalyst) |
|---|---|---|---|---|
| 6 | 0.5 | 0.99 | 71 | 0.27 |
| 7 | 0.75 | 0.90 | 68 | 0.21 |
| 8 | 0.75 | 0.95 | 78 | 0.24 |

EXAMPLES 9-11

Three catalysts were prepared by adding an ethanol solution of tantalum ethoxide to ATM using the excess solvent procedure followed by decomposing the tantalum-loaded ATM to molybdenum sulfide, then impregnating the tantalum-loaded molybdenum sulfide with an aqueous solution of potassium acetate by incipient wetness and calcining the potassium impregnated catalyst. Test results are reported in Table 4.

TABLE

| Cat. No. | Mole Ta per 100 moles Mo | Mole K per mole Mo | Density (g/cc) | Alcohol Selectivity (%) | Alcohol Production Rate (lb alcohol/hr/lb cat.) |
|---|---|---|---|---|---|
| 9 | 0.82 | 0.5 | 1.12 | 69 | 0.29 |
| 10 | 0.82 | 1.0 | 0.69 | 77 | 0.38 |
| 11 | 4.3 | 0.75 | 0.79 | 75 | 0.29 |

EXAMPLES 12-15

Using the same procedures as in Examples 9-11, four catalysts were prepared using a tantalum loading of 0.83 mole Ta per 100 moles Mo and a potassium loading of 0.5 mole K per mole Mo. Two of the catalysts (Exs. 12 and 13) were calcined after potassium impregnation and two were not (Exs. 14 and 15). Test results are reported in Table 5.

TABLE 5

| Catalyst No. | Density (g/cc) | Alcohol Selectivity (%) | Alcohol Production Rate (lb alcohol/hr/lb catalyst) |
|---|---|---|---|
| 12 | 1.15 | 67 | 0.27 |
| 13 | 1.14 | 72 | 0.23 |
| 14 | 0.86 | 73 | 0.36 |
| 15 | 0.78 | 73 | 0.38 |

EXAMPLES 16 AND 17

Using the same procedure as in Examples 9-11, two catalysts were prepared using a tantalum loading of 0.82 mole Ta per 100 moles Mo and potassium loadings of 0.75 and 0.78 mole K per mole Mo, respectively. Test results are reported in Table 6.

TABLE 6

| Catalyst No. | Density (g/cc) | Alcohol Selectivity (%) | Alcohol Production Rate (lb alcohol/hr/lb catalyst) |
|---|---|---|---|
| 16 | 0.87 | 74 | 0.34 |
| 17 | 0.65 | 80 | 0.39 |

EXAMPLE 18

Using the procedures of Examples 9-11, a catalyst was prepared having 0.86 mole Ta per 100 moles Mo, 0.70 mole K per mole Mo and a density of 0.84 g/cc. Upon testing, this catalyst provided an alcohol selectivity of 78% and an alcohol production rate of 0.32 lb alcohol/hr/lb catalyst.

EXAMPLES 19-22

Three catalysts were prepared using the procedures of Examples 9-11. The catalysts all had a tantalum loading of 0.83 mole Ta per 100 moles Mo and a potassium loading of 0.75 K per mole Mo. The catalyst of Example 21 was not calcined after potassium impregnation. Test results are reported in Table 7.

TABLE 7

| Catalyst No. | Density (g/cc) | Alcohol Selectivity (%) | Alcohol Production Rate (lb alcohol/hr/lb catalyst) |
|---|---|---|---|
| 19 | 0.71 | 80 | 0.41 |
| 20 | 0.72 | 78 | 0.38 |
| 21 | 0.69 | 77 | 0.36 |

EXAMPLE 22

The catalyst of Example 19 was formed into pellets and tested. The pelleted catalyst exhibited a density of 1.20 g/cc, an alcohol selectivity of 70% and an alcohol production rate of 0.27 lb alcohol/hr/lb catalyst.

EXAMPLE 23

A catalyst was prepared by impregnating ATM with an aqueous solution of tantalum oxalate via the incipient wetness technique to provide 0.82 mole Ta per 100 moles Mo. After decomposing the tantalum-loaded ATM to molybdenum sulfide, an aqueous solution of potassium acetate was added via incipient wetness to provide 0.75 mole K per mole Mo, and the catalyst was then calcined. On testing, the catalyst exhibited a density of 0.9 g/cc, an alcohol selectivity of 72% and an alcohol production rate of 0.32 lb alcohol/hr/lb catalyst.

It will be noted that some of the catalysts of the present invention consisting essentially of molybdenum sulfide, potassium and tantalum (e.g. Examples 2, 5, 8, 11) provided a higher alcohol selectivity than the average results obtained using the optimized, prior art catalyst consisting of only molybdenum sulfide and potassium; other catalysts of the invention provided a higher alcohol production rate (e.g. Examples 14, 15 and 23); while still others were superior both in terms of alcohol selectivity and alcohol production rate (e.g. Examples 10, 16, 17, 18, 19, 20 and 21). While some of the catalysts (e.g. Examples 1, 3, 4, 6–7, 9, 12–13 and 22) did not exhibit superior performance in the reported tests, it must be recognized that no attempt was made to optimize performance of these examples. Such optimization could well lead to improved results. More importantly, even these less desirable examples of the present invention exhibited enhanced activities and/or selectivities relative to other known catalysts for converting synthesis gas to alcohols.

Although the invention has been described in its preferred forms with a certain degree of particularity, it is understood that various modifications will occur to those skilled in the art and that such modifications are included within the purview of this application and the spirit and scope of the appended claims.

I claim:

1. A catalyst useful for converting carbon monoxide and hydrogen to a mixture of alcohols, wherein the catalyst consists essentially of a mixture of molybdenum sulfide, an alkali metal compound and a tantalum compound.

2. The catalyst of claim 1 wherein the alkali metal compound is selected from organic and inorganic salts, oxides, sulfides and hydroxides of alkali metals.

3. The catalyst of claim 2 wherein said inorganic salt is potassium acetate.

4. The catalyst of claim 1 wherein the alkali metal compound is present in the catalyst in an amount to provide from 0.30 mole to 2 moles alkali metal per mole of molybdenum.

5. The catalyst of claim 4 wherein the alkali metal compound is potassium acetate.

6. The catalyst of claim 4 wherein the tantalum compound is present in the catalyst in an amount to provide from 0.3 mole to 10 moles of tantalum per 100 moles of molybdenum.

7. The catalyst of claim 6 wherein the tantalum compound is selected from tantalum oxalate, tantalum ethoxide and mixtures thereof.

8. The catalyst of claim 7 wherein said catalyst is obtained by decomposing a tantalum-impregnated tetrathiomolybdate salt to obtain tantalum-impregnated molybdenum sulfide and then the alkali metal compound is added to said tantalum-impregnated molybdenum sulfide.

* * * * *